United States Patent
Calatzis et al.

(10) Patent No.: US 10,909,213 B2
(45) Date of Patent: *Feb. 2, 2021

(54) SUPPLEMENTING MEASUREMENT RESULTS OF AUTOMATED ANALYZERS

(71) Applicant: Roche Diagnostics Operations, Inc., Indianapolis, IN (US)

(72) Inventors: Andreas Calatzis, Rotkreuz (CH); Felix Dross, Kirchhain (DE); Marianne Wilmer, Root (CH); Simon John Davidson, Steinhausen (CH)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 298 days.

This patent is subject to a terminal disclaimer.

(21) Appl. No.: 15/810,788

(22) Filed: Nov. 13, 2017

(65) Prior Publication Data

US 2018/0143944 A1 May 24, 2018

(30) Foreign Application Priority Data

Nov. 23, 2016 (EP) ..................................... 16200295

(51) Int. Cl.
*G06F 17/18* (2006.01)
*G16H 10/40* (2018.01)
*G06F 19/00* (2018.01)
*G06F 21/62* (2013.01)

(52) U.S. Cl.
CPC .......... *G06F 17/18* (2013.01); *G06F 19/3418* (2013.01); *G06F 21/6254* (2013.01); *G16H 10/40* (2018.01)

(58) Field of Classification Search
None
See application file for complete search history.

(56) References Cited

U.S. PATENT DOCUMENTS

| 7,286,997 | B2 | 10/2007 | Spector et al. |
| 7,698,154 | B2 | 4/2010 | Marchosky |
| 8,515,887 | B2 | 8/2013 | Lord et al. |
| 8,600,830 | B2 * | 12/2013 | Hoffberg ............... G07F 17/323 705/26.3 |
| 8,655,682 | B2 | 2/2014 | Srivastava et al. |

(Continued)

FOREIGN PATENT DOCUMENTS

WO 2005/034001 A1 4/2005

*Primary Examiner* — Tung S Lau
(74) *Attorney, Agent, or Firm* — Roche Diagnostics Operations, Inc.

(57) ABSTRACT

A computer-implemented method for supplementing measurement results of automated analyzers is presented. The method includes obtaining, at a computer device, a result of a measurement performed by an automated analyzer, the computer device and the automated analyzer being located within a privileged computer network, obtaining a context related algorithm associated with the result of the measurement defining one or more triggering conditions and context related information from a computer device residing outside of the privileged computer network at the computer device and processing the result of the measurement by using the context related algorithm to generate a context specific supplement to the result of the measurement at the computer device.

11 Claims, 3 Drawing Sheets

(56) References Cited

U.S. PATENT DOCUMENTS

| | | | |
|---|---|---|---|
| 2003/0070003 A1* | 4/2003 | Chong | H04L 63/1408 |
| | | | 719/330 |
| 2006/0293784 A1* | 12/2006 | Braunstein | G07F 11/002 |
| | | | 700/231 |
| 2007/0087756 A1* | 4/2007 | Hoffberg | G06Q 10/0635 |
| | | | 455/450 |
| 2008/0300919 A1* | 12/2008 | Charlton | A61B 5/14532 |
| | | | 705/2 |
| 2009/0287837 A1* | 11/2009 | Felsher | G06Q 10/10 |
| | | | 709/229 |
| 2010/0005344 A1 | 1/2010 | Gyles et al. | |
| 2011/0245089 A1 | 10/2011 | Scott et al. | |
| 2012/0042214 A1 | 2/2012 | Jacobs et al. | |
| 2018/0080949 A1* | 3/2018 | Jost | G01N 35/0092 |
| 2018/0143944 A1* | 5/2018 | Calatzis | G06F 19/3418 |
| 2018/0373622 A1* | 12/2018 | Puig | G16H 10/40 |
| 2020/0150138 A1* | 5/2020 | Buller | B01L 1/00 |
| 2020/0191813 A1* | 6/2020 | Bechmann | G01N 35/00 |

* cited by examiner

SUPPLEMENTING MEASUREMENT RESULTS OF AUTOMATED ANALYZERS

CROSS-REFERENCE TO RELATED APPLICATIONS

This application is based on and claims priority to EP 16200295.0, filed Nov. 23, 2016, which is hereby incorporated by reference.

BACKGROUND

The present disclosure relates to methods and systems for supplementing measurement results of automated analyzers.

Automated analyzers play an important role in today's laboratory environments. The measurement results of these automated analyzers are used, e.g., by medical practitioners, to make therapy decisions. Even though medical practitioners are usually highly trained, errors might happen in the process of interpreting the measurement result of automated analyzers. These errors can lead to grave consequences for the patient.

SUMMARY

According to the present disclosure, a computer-implemented method for supplementing measurement results of diagnostic or laboratory automated analyzers is presented. The method can comprise obtaining, at a computer device, a result of a measurement performed by a diagnostic or laboratory automated analyzer. The computer device and the automated analyzer can be located within a privileged computer network. The method can also comprise obtaining a context related algorithm associated with the result of the measurement defining one or more triggering conditions and context related information from another computer device that resides outside of the privileged computer network at the computer device and processing the result of a measurement by the diagnostic or laboratory automated analyzer by using the context related algorithm to generate a context specific supplement to the result of the measurement at the computer device.

Other features of the embodiments of the present disclosure will be apparent in light of the description of the disclosure embodied herein.

BRIEF DESCRIPTION OF THE SEVERAL VIEWS OF THE DRAWINGS

The following detailed description of specific embodiments of the present disclosure can be best understood when read in conjunction with the following drawings, where like structure is indicated with like reference numerals and in which.

DETAILED DESCRIPTION

Figure 1:
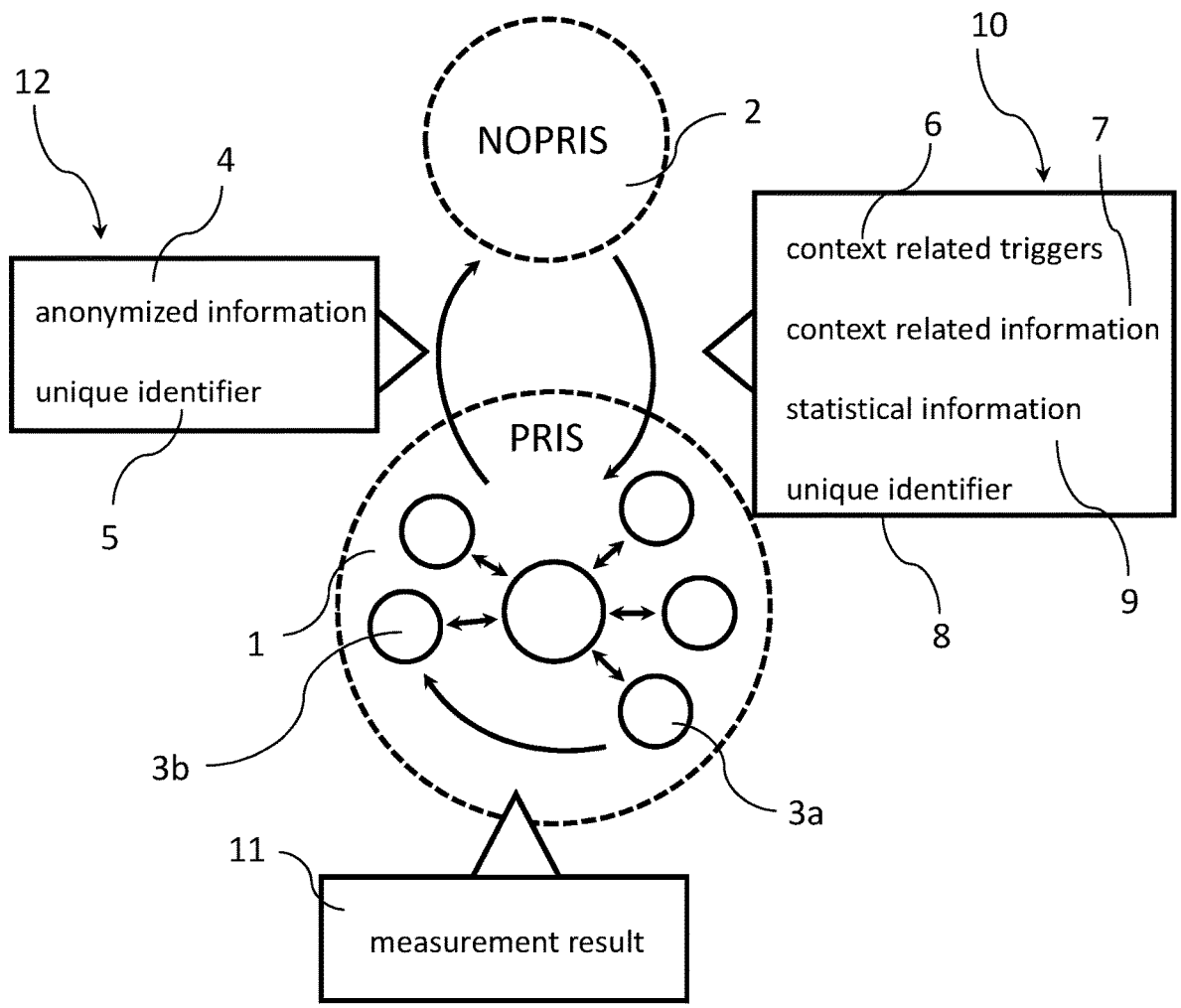
FIG. 1 illustrates schematically an exchange of information between computer devices inside and outside a privileged computer network according to an embodiment of the present disclosure.

In the following detailed description of the embodiments, reference is made to the accompanying drawings that form a part hereof, and in which are shown by way of illustration, and not by way of limitation, specific embodiments in which the disclosure may be practiced. It is to be understood that other embodiments may be utilized and that logical, mechanical and electrical changes may be made without departing from the spirit and scope of the present disclosure.

A computer-implemented method for supplementing measurement results of automated analyzers is presented. The method can include obtaining, at a computer device, a result of a measurement performed by an automated analyzer, the computer device and the automated analyzer being located within a privileged computer network, obtaining a context related algorithm associated with the result of the measurement defining one or more triggering conditions and context related information from a computer device residing outside of the privileged computer network at the computer device and processing the result of the measurement by using the context related algorithm to generate a context specific supplement to the result of the measurement at the computer device. A computer network can be configured to carry out the above method.

Some advantages of the above method can be, firstly, the method can render measurement results issued by automated analyzers more informative by adding context specific supplements. This, in turn, may improve a quality of therapy or other decisions based on the measurement results and/or reduce a number of errors when the measurement results are interpreted in some examples.

Secondly, the method can improve quality context specific supplements provided by automated analyzers in some examples. For example, an automated analyzer may only use algorithms authored by certain sources to supplement its measurement results.

Thirdly, the method can allow for updating the algorithms used by automated analyzers in a simpler manner in some examples. In some prior art automated analyzers, algorithms used to supplement measurement results are included in the instrument software delivered with an instrument. However, this software might not be updated regularly and/or an operator might have no influence on the content of the updates. The method can facilitate a continuous update process of specific and selected algorithms for generating supplements to measurement results in some examples.

Fourthly, the method can allow for using software developed on private data (e.g., patient data) in other networks located outside a privileged network the software is developed in (e.g., a hospital or laboratory network). In this matter, a knowledge base used to supplement the measurement results of the automated analyzer can be increased in some examples. This may further improve a usefulness of the generated supplements.

Fifthly, the method can involve collecting and using statistical data in supplements of measurement results of automated analyzers which can also improve the usefulness of these results.

The term 'diagnostic or laboratory automated analyzer' as used herein can refer to any kind of automated or semi-automated technical device to generate measurement results in a laboratory or other health-care related environment.

The term 'diagnostic automated analyzer' can not only include automated analyzers used in the process of diagnosing a disease, but also automated analyzers for screening, health classification, risk assessment, monitoring, staging, prediction, prognosis and more. For example, a diagnostic automated analyzer can be an ultrasound device, a radiology device (e.g., an x-ray device, a computer tomography device or a MRI device), an ECG device or an EEG device or another monitoring device of a bodily function.

A 'laboratory automated analyzer' can be any automated analyzer used in laboratory work in the clinical, chemical, biological, immunology or pharmaceutical area or the like. For example, 'automated analyzers' can include in-vitro diagnostic analyzers, 'Automated analyzers' may not be necessarily is located in a dedicated laboratory or clinical environment. Rather, the term can also include stand-alone analyzers for carrying out diagnostic or analytic procedures in the clinical, chemical, biological, immunology or pharmaceutical area. For example, a benchtop device in point-of-care settings such as physician clinics or pharmacies or a device for home-use can also be a piece of laboratory equipment according to the present disclosure.

'Automated analyzers' as used herein can comprise a control unit or controller operatively coupled to one or more analytical, pre- and post-analytical work cells. The control unit can be operable to control the work cells. In addition, the control unit may be operable to evaluate and/or process gathered analysis data, to control the loading, storing and/or unloading of samples to and/or from any one of the analyzers, to initialize an analysis or hardware or software operations of the analysis system used for preparing the samples, sample tubes or reagents for the analysis and the like.

The term 'analyzer'/'analytical work cell' as used herein can encompass any apparatus, or apparatus component, that can induce a reaction of a biological sample with a reagent for obtaining a measurement value. An analyzer can be operable to determine via various chemical, biological, physical, optical or other technical procedures a parameter value of the sample or a component thereof. An analyzer may be operable to measure the parameter of the sample or of at least one analyte and return the obtained measurement value. The list of possible analysis results returned by the analyzer can comprise, without limitation, concentrations of the analyte in the sample, a digital (yes or no) result indicating the existence of the analyte in the sample (corresponding to a concentration above the detection level), optical parameters, DNA or RNA sequences, data obtained from mass spectroscopy of proteins or metabolites and physical or chemical parameters of various types. An analytical work cell may comprise units assisting with the pipetting, dosing, and mixing of samples and/or reagents. The analyzer may comprise a reagent holding unit for holding reagents to perform the assays. Reagents may be arranged for example in the form of containers or cassettes containing individual reagents or group of reagents, placed in appropriate receptacles or positions within a storage compartment or conveyor. It may comprise a consumable feeding unit. The analyzer may comprise a process and detection system whose workflow can be optimized for certain types of analysis. Examples of such analyzer are clinical chemistry analyzers, coagulation chemistry analyzers, immunochemistry analyzers, urine analyzers, nucleic acid analyzers, used to detect the result of chemical or biological reactions or to monitor the progress of chemical or biological reactions.

The term 'privileged (computer) network' as used herein can refer to any computer network having a barrier between it and another outside network. The privileged computer network can be a trusted, secure internal network and the other outside network, such as the Internet, can be assumed not to be secure or trusted. A privileged (computer) network can be protected by a firewall or another network protection means.

For example, a privileged (computer) network can be a hospital network or a laboratory network (also referred to as 'hospital information system' and 'laboratory information system' herein). In these examples, patient data or similar data can be accessible at computer devices within the privileged (computer) network (possibly subject to authentication or other access requirements) but not from a computer device outside the privileged (computer) network.

Accordingly, the term 'non-privileged (computer) network' as used herein can refer to any computer network which is not a privileged computer network.

The term 'computer network' as used herein can encompass any type of wireless network, such as a WIFI, GSM, UMTS or other wireless digital network or a cable based network, such as Ethernet or the like. In particular, the communication network can implement the Internet protocol (IP). For example, the communication network can comprise a combination of cable-based and wireless networks.

A 'control unit' or 'controller' can control the automated or semi-automated system in a way that the necessary steps for the processing protocols can be conducted by the automated system. That can mean the control unit may, for example, instruct the automated system to conduct certain pipetting steps to mix the liquid biological sample with reagents, or the control unit can control the automated system to incubate the sample mixtures for a certain time and the like. The control unit may receive information from a data management unit regarding which steps may need to be performed with a certain sample. In some embodiments, the control unit may be integral with the data management unit or may be embodied by a common hardware. The control unit may, for instance, be embodied as a programmable logic controller running a computer-readable program provided with instructions to perform operations in accordance with a process operation plan. The control unit may be set up to control, for example, any one or more of the following operations: loading and/or wasting and/or washing of cuvettes and/or pipette tips, moving and/or opening of sample tubes and reagent cassettes, pipetting of samples and/or reagents, mixing of samples and/or reagents, washing pipetting needles or tips, washing mixing paddles, controlling of a light source, e.g. selection of the wavelength, or the like. In particular, the control unit may include a scheduler, for executing a sequence of steps within a predefined cycle time. The control unit may further determine the order of samples to be processed according to the assay type, urgency, and the like.

A 'measurement result' of the diagnostic or laboratory automated analyzer as used herein can be any output the above listed automated analyzer. Depending on the respective automated analyzer, a measurement result can be obtained by analyzing live or dead body or a part thereof (e.g., a mammalian patient or a part of a mammalian patient) or a sample (e.g., a biological sample).

For instance, a measurement result can include one or more parameter values measured in a live or dead body or a part thereof or a sample (e.g., a concentration of a particular substance in a blood sample). In other examples, a measurement result can include one or more images of a live or dead body or a part thereof or a sample (e.g., an X-ray or MRI image).

The term 'sample' can refer to material(s) that may potentially contain an analyte of interest. The sample can be derived from a biological source, such as a physiological fluid, including blood, saliva, ocular lens fluid, cerebrospinal fluid, sweat, urine, stool, semen, milk, ascites fluid, mucous, synovial fluid, peritoneal fluid, amniotic fluid, tissue, cultured cells, or the like. The biological sample can be pretreated prior to use, such as preparing plasma from blood. Methods of treatment can involve centrifugation, filtration, distillation, dilution, concentration and/or separation of sample components including analytes of interest, inactivation of interfering components, and the addition of reagents. A sample may be used directly as obtained from the source or used following a pretreatment to modify the character of the sample. In some embodiments, an initially solid or semi-solid biological material can be rendered liquid by dissolving or suspending it with a suitable liquid medium. In some examples, the sample can be suspected to contain a certain antigen or nucleic acid.

The term 'order' can include any request for a piece of laboratory equipment to automatically or semi-automatically carry out a particular task. For example, an order can be a request that one or more assays are to be performed on one or more biological samples.

The methods and systems for supplementing measurement results according to the present disclosure will be discussed in connection with FIG. 1 and FIG. 3. Subsequently, different additional aspects will be discussed in connection with FIG. 2 and FIG. 3.

FIG. 1 schematically illustrates an exchange of information 12, 10 between computer devices 3a, 3b inside and outside a privileged computer network 1 (PRIS) according to the present disclosure. In the example of FIG. 1, the communication can take place with a computer device in a non-privileged computer network 2 (NOPRIS). In the example of FIG. 1, a first computer device 3a can be an automated analyzer (e.g., an in-vitro automated analyzer). A second computer device 3b can be a user terminal in the privileged computer network 1 (PRIS). For example, the user terminal can be a desktop computer or a mobile device (e.g., a tablet device, a laptop or a smartphone). The privileged computer network 1 (PRIS) can be a hospital network or a laboratory network (also referred to as hospital information system (HIS) or laboratory information system (LIS) herein).

It can be noted that the particular devices and networks are only examples of computer devices and networks used for the sake of illustration. The techniques of the present disclosure can also be used in other environments (e.g., as discussed below in connection with FIG. 2).

As can be seen, the method can comprise obtaining (see step 101 in FIG. 3), at the user terminal 3b, a result of a measurement 11 performed by the automated analyzer 3a (e.g., a result of any assay of an in-vitro analyzer or any of the other measurement results discussed above). In a further step (see step 102 in FIG. 3), information regarding the result of the measurement 12 can be transmitted to a computer device residing outside of the privileged computer network 1 in the non-privileged network 2.

However, in other examples, no information regarding the result of the measurement 12 can be provided outside the privileged computer network 1. The techniques of the present disclosure can still be applied without this step (besides the aspects relying on the provision of information regarding the result of the measurement to a computer device in the non-privileged network).

Moreover, the user terminal 3b can receive (see step 103 in FIG. 3) a context related algorithm associated with the result of the measurement defining one or more triggering conditions 6 and context related information 7 from the computer device residing outside of the privileged computer network 1. Then, the user terminal 3b (or another computer device inside the privileged computer network 1) can process (see step 104 in FIG. 3) the result of the measurement by using the context related algorithm to generate a context specific supplement to the result of the measurement 11 at the computer device.

The different steps and elements of the technique for supplementing measurement results according to the present disclosure can subsequently be discussed in more detail.

The information regarding the result of the measurement 12 will be discussed first. As can be seen in FIG. 1, the information regarding the result of the measurement 12 may include anonymized information regarding the result of the measurement 4 and a unique identifier 5.

The anonymized information regarding the result of the measurement 4 can be generated by removing identifying specific information regarding a patient from the measurement result 11 and supplementing the result by a unique identifier and potentially other generic identifiers for the sample. In the following, it can be assumed that the measurement result 11 has been obtained by analyzing a patient or a sample associated with a patient. However, the techniques of the present disclosure may not be limited to situations in which the analysis object is a patient. Other scenarios are, e.g., discussed above.

In other words, the measurement result 11 can be de-identified before being provided to the computer device outside the privileged computer network 1. This process can include removing, encrypting and/or obfuscating any information suitable to identify a patient associated with the measurement result 11. For instance, the anonymization process can include removing or encrypting a name of the patient, an address of the patient, contact data of the patient, a social security or insurance carrier number or other information suitable to identify the patient.

The remaining anonymized information 4 can include one or more of: one or more measurement values determined by the automated analyzer, an image obtained by the automated analyzer and a description of the result of the measurement of the automated analyzer, or meta-data processed based on or one or more of these pieces of information. In one example, anonymized information 4 can include the results of one or more assays conducted on a sample (e.g., an assay of an in-vitro analyzer).

In addition, the anonymized information 4 can include additional information associated with the result of the measurement 11. In one example, the additional information can include clinical information associated with the result of the measurement 11. For instance, the clinical information can include biometric data (e.g., one or more of gender, age, race, height, weight or other biometric data relating to the patient), information regarding physical symptoms and findings of the patient, information regarding the anamnesis and ongoing treatment of the patient (e.g., one or more of past and ongoing treatments, past surgical procedures, prescribed drugs, past or current diagnostic information regarding the patient and other related information).

However, in other examples, some of the clinical information (or all clinical information in some examples) associated with the result of the measurement may not leave the privileged computer network 1. In these examples, such information cannot be provided to the computer device outside the privileged computer network 1. In addition or alternatively, certain clinical information can be used to identify the patient in some examples. Thus, the anonymized information 4 can be free of this type of information in some examples.

In one example, the anonymized information 4 can include the result of any assay or other analytical information obtained by the automated analyzer and information regarding a diagnosis for the patient (e.g., ICD coded information).

In addition or alternatively, the anonymized information 4 can include information regarding the automated analyzer having performed the measurement yielding the measurement result (e.g., an identity of a manufacturer, a model number or a unique identifier of the device). In addition or alternatively, the anonymized information 4 can include information regarding a state of the automated analyzer having performed the measurement yielding the measurement result (e.g., information regarding disposables used by the automated analyzer or measurement parameters used by the automated analyzer).

The unique identifier 5 can be any data item suitable to identify a particular information regarding the result of the measurement 12 sent to the computer device outside the privileged computer network 1.

The computer device residing outside of the privileged computer network (e.g., in the non-privileged computer network 2) can process the information regarding the result of the measurement 12, as will be discussed in more detail below. Before that, in the subsequent sections, the information 10 received at the privileged computer network 1 from the computer device residing outside of the privileged computer network (e.g., in the non-privileged computer network 2) can be explained in more detail.

This information 10 can include a context related algorithm associated with the result of the measurement defining the one or more triggering conditions 6 and context related information 7.

The context related algorithm can be provided as a computer program which can be executed by the user terminal 3a in the privileged computer network 1 to generate a context specific supplement to the result of the measurement 11. For example, the context related algorithm can be provided as a stand-alone program (e.g., an application for a mobile device or a stand-alone program for another a computer device). In other examples, the context related algorithm can be provided as an add-on to a computer program already installed on a compute device in the privileged computer network. For instance, the computer program may be a presentation, or analysis, tool for measurement results of automated analyzers. The context related algorithm can be added to the functionalities of this presentation, or analysis, tool (additional details will be discussed below in connection with the generation of the supplement to the result of the measurement).

In some examples, the context related algorithm can be provided in a form suitable to be transmitted over a network which may need to be further processed at the user terminal 3a in the privileged computer network 1 before it can be used to supplement the measurement results. For instance, it may be necessary to compile, install and/or setup the context related algorithm in some examples. In other examples, the context related algorithm can be provided as executable code.

The one or more triggering conditions 6 can define one or more criteria for the result of the measurement in some examples. In some examples, the one or more criteria can include one or more of: a criterion evaluating a threshold for one or more measurement values, a criterion determining a relationship between two or more measurement values and a criterion defining a pattern in a result of a measurement.

For instance, a triggering condition can be that an analyte concentration in a sample lies below or above a predetermined threshold, or in a predetermined concentration range. In other examples, the triggering condition can be the presence of one or more analytes in a sample. In still other examples, the triggering condition can be the presence of a characteristic in a waveform included in the measurement result (e.g., of an EEG or an EEC waveform). In still other examples, the triggering condition can be the presence of a feature of an image of the measurement result (e.g., a feature in an X-ray or MRI image).

In still other examples, the one or more triggering conditions 6 can define criteria not only for the measurement result 11 but also for results of additional measurements (e.g., a second analyte concentration being the measurement result of another assay). In other words, the one or more triggering conditions 6 can define criteria for a combination of measurement results of different sources, or of the same source at different times (e.g., a first assay at an earlier time and a second assay of the same type at a later time).

In addition or alternatively, the one or more triggering conditions 6 can define criteria for clinical data and/or other patient data associated with the measurement result 11 (e.g., the clinical and/or patient data discussed above). For example, a triggering condition 6 can define a criterion for the measurement result 11 and biometric data associated with the patient (or other patient data). An example of this triggering condition may include a first criterion regarding the result of an assay (e.g., concentration of analyte X is above a threshold value) and a second criterion regarding patient data (e.g., patient is older than threshold age Y). In other words, the triggering conditions 6 can define criteria for a combination of measurement results with clinical and/or patient data.

Subsequently, the context related information 7 defined by the context related algorithm will be discussed in more detail. The context related information 7 can include one or more of: explanatory information regarding the interpretation of the measurement result of the automated analyzer, proposals regarding diagnostic steps to be undertaken (e.g., proposals regarding additional measurements to be carried out), proposals regarding treatment steps to be carried out, information regarding potential errors that occurred while performing the measurement by the automated analyzer, or additional information related to the measurement result or clinical data associated with the measurement result.

In one illustrative example, the measurement result 11 is an international normalized ratio (INR) determined by a coagulation analyzer. A particular context related algorithm can include a triggering condition defining a particular INR range (e.g., INR>2 and INR<3) and define a context related information 7 associated with the triggering condition in the form of a textual information "INR is in the therapeutic range for preventive oral anticoagulation with Wafarin." In this example, the measurement result including an INR for a patient may be supplemented with this textual information when the measurement result 11 is processed by using the context related algorithm. This process will be explained in more detail.

As discussed above, the technique of present disclosure can include processing the result of the measurement by using the context related algorithm to generate a context specific supplement to the result of the measurement at the computer device. It has been discussed above (further details will be discussed below) that one or more context related algorithms can be obtained at a computer device (e.g., user terminal 3a) inside the privileged computer network 1. In one example, a plurality of context related algorithms can be obtained from the computer device outside the privileged computer network 1 and provided for use inside the privileged computer network 1.

The computer devices of the privileged computer network 1 (e.g., user terminal 3a or another computer device located inside the privileged computer network 1) can now apply the context related algorithms to process a result of a measurement by a diagnostic or laboratory automated analyzer in the privileged computer network 1.

This can involve checking if a triggering condition is met by the result of a measurement 11. As discussed above, this can include processing (see step 104 in FIG. 3) the result of a measurement (e.g., a calculation meta-data based on the result of a measurement or feature extraction of features of the result of a measurement).

In other examples, the processing can involve checking if a triggering condition is met by results of additional measurements associated with the result of a measurement (e.g., belonging to the same patient). Alternatively or in addition, the processing can involve checking if a triggering condition is met by clinical or other patient data associated with the result of a measurement (e.g., belonging to the same patient). Further examples are discussed above in connection with the triggering conditions 6.

If the one or more triggering conditions 6 are met, the context related information 7 can be processed into the context specific supplement to the result of the measurement. In one example, this can involve adding textual information contained in the context related information 7 to the result of the measurement (as in the INR example above). However, the context specific supplement can also include additional or alternative items other than textual information. In one example, the context related supplement can include an audible, visual or audiovisual warning. In another example, the context related supplement can include a hyperlink linking to additional resources (e.g., regarding interpretation of the measurement results or statistical data). In still other examples, the context related supplement can include a further algorithm whose execution can be triggered by a user (e.g., ordering a repeated measurement or further diagnostic steps or an analysis of the measurement result and/or additional clinical data of the patient).

In one example, an indicator can be presented to a user at a computer device 3a inside the privileged computer network 1 that a context specific supplement is available for the result of the measurement on a user interface of the computer device 3a. For instance, an icon or other indicator may be displayed on a user interface of the computer device 3a. In response to a user interaction with the user interface of the computer device (e.g., pressing the icon or hovering over the icon), the context specific supplement can be presented to a user (see step 105 in FIG. 3). In other examples, the context specific supplement can be automatically presented to a user when an associated measurement result is presented (e.g., on a graphical user interface of the automated analyzer or another device in the privileged computer network).

In one example, the processing of the result of the measurement using the context related algorithm can be performed automatically (i.e., without user interaction).

In the following passages, additional details regarding process to retrieve context specific algorithms will be discussed.

In one example, one or more context related algorithms can be obtained automatically from the computer device residing outside of the privileged computer network 1. The process of obtaining the context related algorithms can happen continuously. For example, context related algorithms can be obtained at predetermined points in time or upon occurrence of a predetermined event (e.g., when an automated analyzer performs a particular measurement).

In another example, the computer device residing outside of the privileged computer network 1 (e.g., in the non-privileged network 2) can be continuously or regularly checked for new or updated context related algorithms. Then, if a new or updated context related algorithm is available at the computer device residing outside of the privileged computer network 1 (e.g., in the non-privileged network 2), this context related algorithm can be retrieved by a computer device inside the privileged computer network 1.

In other examples, a user inside the privileged computer network 1 may have to confirm that context related algorithms can be obtained. In still other examples, a user inside the privileged computer network 1 may access a user interface presented by the computer device of outside of the privileged computer network 1 and select one or more context related algorithms to be obtained.

In addition or alternatively, a user inside the privileged computer network 1 can select one or more sources whose context related algorithms can be obtained at the computer device 3a. In these cases, context related algorithms from the selected one or more sources (e.g., a particular author of context related algorithms) can be obtained if they are available at the computer device residing outside of the privileged computer network 1 (e.g., in the non-privileged network 2), e.g., continuously or upon a predetermined trigger event. In other words, a user can subscribe context related algorithms of one or more sources. Further explanations regarding this aspect will be given in connection with FIG. 2.

In one example, the computer device residing outside of the privileged computer network 1 (e.g., in the non-privileged network 2) can include a repository of context related algorithms defining one or more triggering conditions and context related information. For instance, the context related algorithms in the repository may have been created in privileged computer networks other than the privileged computer system 1. In this manner, the users inside the privileged computer system 1 can gain access to a large number of context related algorithms which can be update in a regular manner.

It has been explained above that the context specific supplement can include particular information derived from the context related information of a context related algorithm. In addition or alternatively, the context specific supplement can also include statistical information 9 associated with the result of the measurement.

In one example, the statistical information associated with the result of the measurement can include information regarding a likelihood of a combination of measurement values in the result of the measurement with other measurement values. For instance, the statistical information may indicate that the results of two different measurements of the same sample or associated to the same patient have a likelihood being below a predetermined threshold. By adding this statistical information to a supplement of a measurement result, a user may be able to identify erroneous results.

In addition or alternatively, the statistical information associated with the result of the measurement can include information regarding a likelihood of a combination of a measurement value in the result of the measurement with a particular diagnosis. For instance, the statistical data may indicate that a particular diagnosis is not compatible with a predetermined measurement result (e.g., a combined likelihood of the diagnosis being correct and the measurement result being as it is below a predetermined threshold). In other examples, the statistical information may include a list of one or more likely and/or one or more unlikely diagnoses compatible with the particular measurement result.

In addition or alternatively, the statistical information associated with the result of the measurement can include information regarding a likelihood of a combination of a measurement value of the result with a particular diagnosis or clinical finding. As in the examples above, the data may indicate that a particular diagnosis or clinical finding is not compatible with a predetermined measurement result, or a list of one or more likely and/or one or more unlikely disease progressions or clinical findings compatible with the particular measurement result.

In addition or alternatively, the statistical information associated with the result of the measurement can include information regarding a likelihood of a combination of a measurement value of the result of the measurement with particular biometric data (e.g., of the same patient). As in the examples above, the data may indicate that a particular value biometric data is not compatible with a predetermined measurement result or a list of one or more likely and/or one or more unlikely values of ranges or values of biometric data compatible with the particular measurement result.

In addition or alternatively, the statistical information associated with the result of the measurement statistical information regarding other measurements carried out in combination with the measurement having yielded the result. In this example, the supplement to the measurement result can include one or more propositions for additional measurements to be carried out.

In addition or alternatively, the statistical information associated with the result of the measurement statistical information regarding next diagnostic steps carried out after the measurement having yielded the result. In this example, the supplement to the measurement result can include one or more propositions for additional diagnostic steps.

As can be seen in the above examples, the supplement to the measurement result can include multiple different items of statistical information related to the result of the measurement. A medical practitioner or other user may find this statistical information helpful to interpret the measurement results of automated analyzers.

In the above examples, the statistical information can relate to clinical information contained in or related to the measurement result. In addition or alternatively, the statistical information associated with the context related algorithm can include meta-data regarding the context related algorithm. For example, the statistical information can include one or more of: information regarding a frequency with which a particular context related algorithm has been obtained and statistical information related to a source of the particular context related algorithm. This information can also be added to the context related supplement. In this manner, a user may get additional information regarding a quality and/or trustworthiness of the statistical information. In other examples (or in addition), statistical information regarding context related algorithms can be presented on a user interface of the computer device outside the privileged computer network hosting the repository of context related algorithms.

In connection with FIG. 2 different possible processes to collect the statistical information will be described in more detail.

In the preceding sections, aspects of the interaction of a computer device located in one privileged computer network to obtain context specific algorithms have been discussed in connection with FIG. 1. Subsequently, in connection with FIG. 2, different techniques involving users in multiple privileged computer networks will be treated in more detail, as well as aspects of the generation of context specific algorithms and statistical information.

Figure 2:
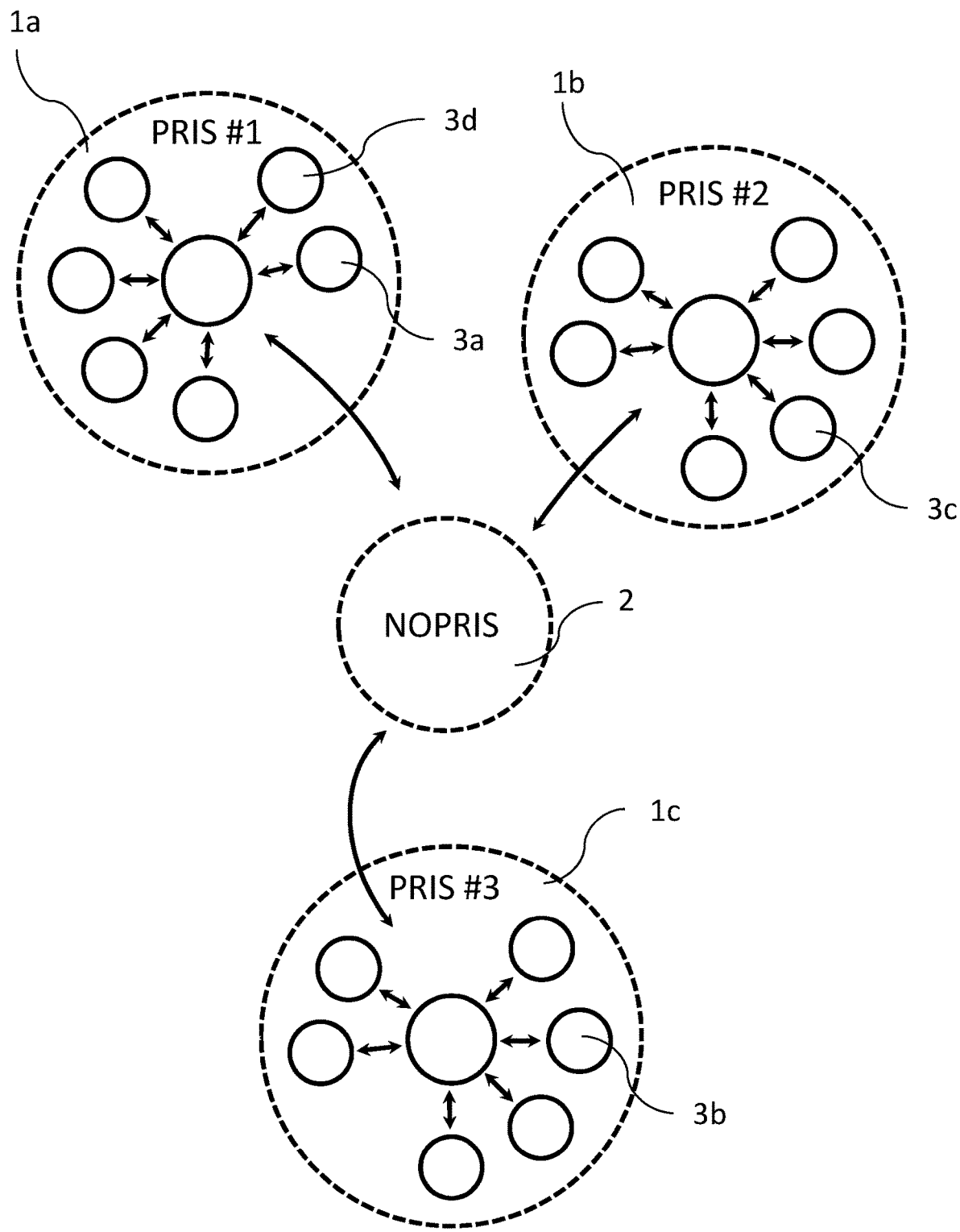
FIG. 2 illustrates a schematic diagram a network environment according to an embodiment of the present disclosure.
Figure 3:
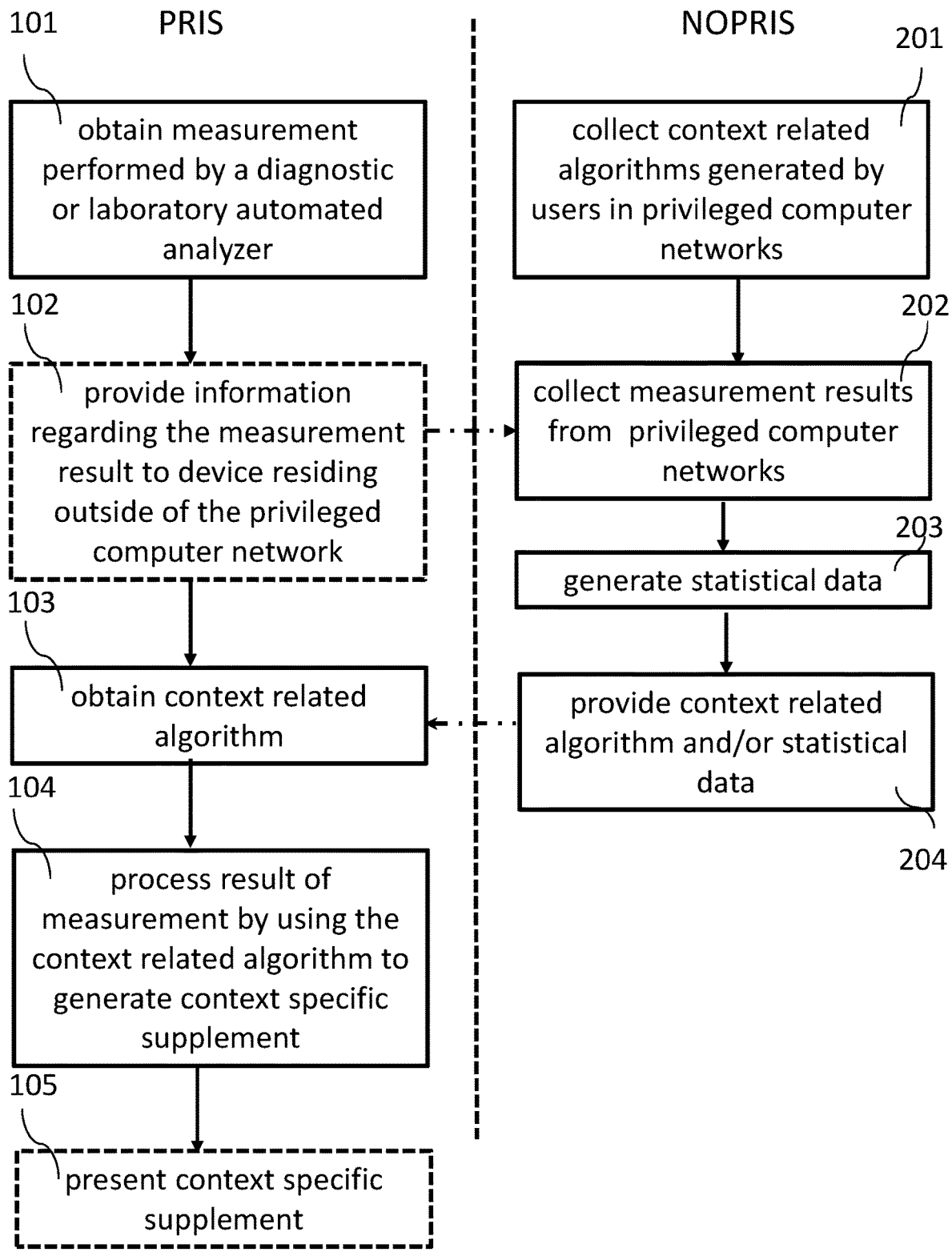
FIG. 3 illustrates a swim lane diagram illustrating the methods according to an embodiment of the present disclosure.

As can be seen in FIG. 2, the computer device residing in the non-privileged network 2 can be networked with multiple privileged computer networks 1a-1c (PRIS #1, PRIS #2, and PRIS #3). Each of the multiple privileged computer networks 1a-1c can be configured as described for the privileged computer network 1 of FIG. 1 above. For instance, each of the multiple privileged computer networks 1a-1c can be a hospital information system or a laboratory information system. Users in each of the multiple privileged computer networks 1a-1c may obtain context related algorithms and statistical information from the computer device residing in the non-privileged network 2 (e.g., from a repository provided by the computer device residing in the non-privileged network 2).

In addition, the techniques of the present disclosure can allow for distributing content between different privileged computer networks 1a-1c. For example, a user in a first privileged computer network (e.g., PRIS #1) can create one or more context related algorithms and provide them to the computer devices residing in the non-privileged network 2. In the same manner, the computer device residing in the non-privileged network 2 can collect context related algorithms generated by other users in other privileged computer networks (e.g., PRIS #2 and PRIS #3 in the example of FIG. 2).

Thus, a repository of context related algorithms at the computer device residing in the non-privileged network 2 may include a multitude of context related algorithms from different sources. A user in any of the privileged computer networks 1a-1c may create context related algorithms using the clinical and patient data available in the respective privileged computer network 1a-1c and upload into the repository. These context related algorithms can then be obtained by users in the other privileged computer networks 1a-1c (or the same privileged computer network 1a-1c). In other words, the computer device residing in the non-privileged network 2 can collect context related algorithms generated by users in multiple privileged computer networks (see also step 201 in FIG. 3).

In one example, a context related algorithm can be associated with a digital identifier identifying a source of the context related algorithm (e.g., a digital signature). In this manner, a user in a different privileged computer network can identify the source the context related algorithm. As explained above, a user can select the context related algorithms to be obtained (at least partially) based on the identity of the creator of the context related algorithm. In some examples, a user can subscribe context related algorithm from one or more particular sources. The digital identifier identifying a source of the context related algorithm can identify one or more of a particular person or group of persons being the creator of the context related algorithm or an organization or institution providing the context related algorithm (e.g., a particular laboratory, hospital or manufacturer of automated laboratory equipment).

The repository of context related algorithms at the computer device residing in the non-privileged network 2 can be configured to allow for a continuous upload of context related algorithms. In this manner, the repository of context related algorithms can be continuously supplemented.

In addition or alternatively, the computer device residing in the non-privileged network 2 can provide a rating system for users to rate the quality of provided context related algorithms (e.g., a star rating or a grade). In addition or alternatively, the computer device residing in the non-privileged network 2 can provide a platform to include comments or additional information regarding provided context related algorithms. The users of the repository can access the rating and/or the comments to judge quality and usefulness of the respective context related algorithms. This may be helpful to improve the value of the context related algorithms for the particular users.

In general, the computer device residing in the non-privileged network 2 can provide an interface to access the context related algorithms in the repository and additional information (e.g., ratings or comments). In one example, the interface may be web-based interface. In other examples, the computer devices of the privileged computer network can interface with the repository on the computer device residing in the non-privileged network 2 via an interface (e.g., an API). In some examples, the interface with the repository can be integrated into a hospital or laboratory information system software, or software controlling one or more automated devices. In still other examples, the hospital or laboratory information system software or the software controlling one or more automated devices can interface with the repository automatically to obtain the context related algorithms described herein. In the following sections, the generation of statistical data (as described above) in network including multiple privileged computer networks will be discussed.

As explained above, (anonymized) information regarding measurement results can be provided to the computer device residing in the non-privileged network 2 from other devices in privileged sources.

In this manner, the computer device residing in the non-privileged network 2 can receive information regarding a plurality of results of a plurality of measurements of automated analyzers located in different privileged computer networks 1a-1c. In addition, the computer device residing in the non-privileged network 2 can receive clinical data or patient data associated with the plurality of measurements of automated analyzers.

The computer device residing in the non-privileged network 2 can collect (see also step 202 in FIG. 3) this data and generate (see also step 203 in FIG. 3) statistical information associated with the plurality of results based on the information regarding the plurality of results (e.g., the statistical information discussed above).

This statistical information can then be provided (see also step 204 in FIG. 3) to the users to supplement measurement results, as also discussed above.

For example, by collecting information from a plurality of sources unlikely measurement results can be identified. For example, a distribution of measurement values for a predetermined test or assay can be compiled. This can be helpful to identify erroneous measurement results.

In another example, information regarding a particular automated analyzer can be obtained by collecting information from a plurality of sources. This can be helpful, e.g., to detect faulty devices or faulty material (e.g., disposable) used in the devices.

As described above, a user can obtain context related algorithms from the repository outside the privileged computer network or provide context related algorithms to the repository outside the privileged computer networks. In some examples, a user within the privileged computer network can have one or more of the privileges comprising obtaining a context related algorithm for the user, obtaining a context related algorithm for all users within the privileged computer network, providing context related algorithms the user has created to the computer device residing outside of the privileged computer network for storage and distribution to other privileged computer networks and providing context related algorithms stored in the privileged computer network to the computer device residing outside of the privileged computer network for storage and distribution to other privileged computer networks.

In the preceding detailed description multiple examples of methods and systems for supplementing measurement results of automated analyzers. However, the methods and systems for supplementing measurement results of automated analyzers of the present disclosure can also be configured as the following.

A computer-implemented method for supplementing measurement results of diagnostic or laboratory automated analyzers is presented. The method can comprise obtaining at a computer device a result of a measurement performed by a diagnostic or laboratory automated analyzer. The computer device and the automated analyzer can be located within a privileged computer network. The method can also comprise obtaining a context related algorithm associated with the result of the measurement defining one or more triggering conditions and context related information from the computer device residing outside of the privileged computer network at the computer device and processing a result of a measurement by the diagnostic or laboratory automated analyzer by using the context related algorithm to generate a context specific supplement to the result of the measurement at the computer device. The processing of the result of the measurement using the context related algorithm can be performed automatically. The context related algorithm can be obtained automatically from the computer device residing outside of the privileged computer network.

The method can further comprise selecting one or more sources whose context related algorithms can be obtained at the computer device and, before obtaining the context related algorithm, verifying the context related algorithm stems from the selected one or more sources.

The selecting one or more sources can include accessing an interface provided by the computer device residing outside of the privileged computer network.

All context related algorithms from the selected one or more sources can be obtained by the computer device automatically. The context related algorithm can be associated with a digital identifier identifying a source of the context related algorithm. The digital identifier can include a digital signature.

The computer device residing outside of the privileged information system can include a repository of context related algorithms defining one or more triggering conditions and context related information. The context related algorithms in the repository can be created in privileged computer networks.

The method can further comprise creating the context related algorithm at a computer device located in a second privileged computer network different from the privileged computer network. The computer device residing outside of the privileged computer network can also reside outside of the second privileged computer network. The method can also comprise providing the context related algorithm to the computer device residing outside of the privileged computer network for storage and distribution to other privileged computer networks.

The context related algorithm can be created at a computer device located in a second privileged computer network different from the privileged computer network. The computer device residing outside of the privileged computer network can also reside outside the second privileged computer network.

The method can further comprise presenting the context specific supplement to the result of the measurement to a user. The presenting the context specific supplement to the result of the measurement to a user can comprise presenting an indicator to the user that a context specific supplement is available for the result of the measurement on a user interface of the computer device and, in response to a user interaction with the user interface of the computer device, presenting the context specific supplement.

The method can further comprise providing information regarding the result of the measurement to a computer device residing outside of the privileged computer network.

The method can further comprise obtaining statistical information associated with the result of the measurement and adding the statistical information associated with the result of the measurement to the context specific supplement. The statistical information associated with the result of the measurement can include one or more of information regarding: a likelihood of a combination of a measurement values in the result of the measurement with other measurement values, a likelihood of a combination of a measurement value in the result of the measurement with a particular diagnosis, a likelihood of a combination of a measurement value in the result with a particular disease progression or clinical finding, a likelihood of a combination of a measurement value in the result of the measurement with particular biometric data, statistical information regarding other measurements carried out in combination with the measurement having yielded the result.

The method can further comprise obtaining statistical information associated with the context related algorithm and adding the statistical information associated with the context related algorithm to the context specific supplement. The statistical information associated with the context related algorithm can include one or more of information regarding a frequency with which the context related algorithm has been obtained and statistical information related to a source of the context related algorithm.

The method can further comprise receiving at the computer device residing outside of the privileged computer network, information regarding a plurality of results of a plurality of measurements of diagnostic or laboratory automated analyzers located in different privileged computer networks and generating statistical information associated with the plurality of results based on the information regarding the plurality of results.

The method can further comprise evaluating the statistical information associated with the result of the measurement at the computer device and presenting to a user one or more of an indication of likely diagnoses associated with the result of the measurement, an indication of unlikely diagnoses associated with the result of the measurement and an indication of frequently performed next diagnostic steps associated with the result of the measurement.

The information regarding the result of the measurement provided to a computer device residing outside of the privileged computer network can include one or more of one or more measurement values determined by the diagnostic or laboratory automated analyzer, one or more images obtained by the diagnostic or laboratory automated analyzers, a description of the result of the measurement of the diagnostic or laboratory automated analyzer and additional information associated with the result of the measurement. The information regarding the result of the measurement can be anonymized.

The one or more triggering conditions can define one or more criteria for the result of the measurement. The one or more criteria can include one or more of a criterion evaluating a threshold for one or more measurement values, a criterion determining a relationship between two or more measurement values and a criterion defining a pattern in a result of a measurement.

The context related algorithm can be provided in a computer program code which can be executed by the computer device in the privileged computer network to generate a context specific supplement to the result of the measurement.

The privileged computer network including at least the computer device and the diagnostic or laboratory automated analyzer can be protected by a firewall or other network protection. The privileged computer network can be a hospital information system or a laboratory information system.

The result of the measurement can be associated with patient-specific information. The patient specific information can be accessed from within the privileged computer network but not from outside of the privileged computer network.

The diagnostic or laboratory automated analyzer can be one of an in-vitro diagnostic analyzer, an ultrasound analyzer, an radiology device or a monitoring device of bodily functions or properties.

The computer device residing outside of the privileged computer network can be networked with a plurality of different privileged computer networks. The method can further comprise obtaining results of measurements from each of the plurality of different privileged computer networks and providing context related algorithms to each of the plurality of different privileged computer networks.

The processing the result of the measurement by using the context related algorithm to generate a context specific supplement includes processing patient data of a patient with which the result of the measurement can be associated. The processing the result of the measurement by using the context related algorithm to generate a context specific supplement can include processing one or more other results of measurements associated with the result of the measurement.

The providing the information regarding the result of the measurement and/or obtaining a context related algorithm can be triggered by a user interaction.

The context related algorithm can be stored in the privileged computer network for further processing operations of results of measurements.

A user within the privileged computer network can have one or more of the privileges comprising: obtaining a context related algorithm for the user, obtaining a context related algorithm for all users within the privileged computer network, providing context related algorithms the user has created to the computer device residing outside of the privileged computer network for storage and distribution to other privileged computer networks and providing context related algorithms stored in the privileged computer network to the computer device residing outside of the privileged computer network for storage and distribution to other privileged computer networks.

The information regarding the result of the measurement can include a unique identifier. The information regarding the result of the measurement can be free of patient identifiers.

A computer network can include a privileged computer network including a first computer device and a diagnostic or laboratory automated analyzer and a second computer network outside of the privileged computer network. The computer network can be configured to carry out the above method.

A computer-readable medium having instructions encoded thereon which, when executed by one or more computer devices can make the one or more computer devices perform the operations of the above method.

Further disclosed and proposed can be a computer program including computer-executable instructions for performing the method according to one or more of the embodiments enclosed herein when the program can be executed on a computer or computer network. Specifically, the computer program may be stored on a computer-readable data carrier. Thus, specifically, one, more than one or even all of method steps as disclosed herein may be performed by using a computer or a computer network by using a computer program.

Further disclosed and proposed is a computer program product having program code, in order to perform the method according to one or more of the embodiments enclosed herein when the program can be executed on a computer or computer network. Specifically, the program code may be stored on a computer-readable data carrier.

Further disclosed and proposed is a data carrier having a data structure stored thereon, which, after loading into a computer or computer network, such as into a working memory or main memory of the computer or computer network, may execute the method according to one or more of the embodiments disclosed herein.

Further disclosed and proposed is a computer program product with program code stored on a machine-readable carrier, in order to perform the method according to one or more of the embodiments disclosed herein, when the program is executed on a computer or computer network. As used herein, a computer program product can refer to the program as a tradable product. The product may generally exist in an arbitrary format, such as in a paper format, or on a computer-readable data carrier. Specifically, the computer program product may be distributed over a data network.

Further disclosed and proposed is a modulated data signal which contains instructions readable by a computer system or computer network, for performing the method according to one or more of the embodiments disclosed herein.

Referring to the computer-implemented aspects, one or more of the method steps or even all of the method steps of the method according to one or more of the embodiments disclosed herein may be performed by using a computer or computer network. Thus, generally, any of the method steps including provision and/or manipulation of data may be performed by using a computer or computer network. Generally, these method steps may include any of the method steps, typically except for method steps requiring manual work, such as providing the samples and/or certain aspects of performing measurements.

Further disclosed and proposed is a computer or computer network comprising at least one processor. The processor can be adapted to perform the method according to one of the embodiments described in this description.

Further disclosed and proposed is a computer loadable data structure that can be adapted to perform the method according to one of the embodiments described in this description while the data structure is being executed on a computer.

Further disclosed and proposed is a storage medium. A data structure can be stored on the storage medium. The data structure can be adapted to perform the method according to one of the embodiments described in this description after having been loaded into a main and/or working storage of a computer or of a computer network.

It is noted that terms like "preferably," "commonly," and "typically" are not utilized herein to limit the scope of the claimed embodiments or to imply that certain features are critical, essential, or even important to the structure or function of the claimed embodiments. Rather, these terms are merely intended to highlight alternative or additional features that may or may not be utilized in a particular embodiment of the present disclosure.

Having described the present disclosure in detail and by reference to specific embodiments thereof, it will be apparent that modifications and variations are possible without departing from the scope of the disclosure defined in the appended claims. More specifically, although some aspects of the present disclosure are identified herein as preferred or particularly advantageous, it is contemplated that the present disclosure is not necessarily limited to these preferred aspects of the disclosure.

We claim:

1. A computer-implemented method for supplementing measurement results of diagnostic or laboratory automated analyzers, the method comprising:

obtaining, at a computer device, a result of a measurement performed by a diagnostic or laboratory automated analyzer, wherein the computer device and the automated analyzer are located within a privileged computer network, and wherein the result of a measurement includes a parameter value of a sample or a component thereof determined by the diagnostic or laboratory automated analyzer;

obtaining a context related algorithm associated with the result of the measurement defining one or more triggering conditions and context related information from another computer device that resides outside of the privileged computer network at the computer device;

processing the result of a measurement by the diagnostic or laboratory automated analyzer by using the context related algorithm to generate a context specific supplement to the result of the measurement at the computer device including processing the context related information into a context specific supplement to the result of the measurement if the one or more triggering conditions are met;

obtaining results of measurements from each of the plurality of different privileged computer networks; and providing context related algorithms to each of the plurality of different privileged computer networks, wherein the measurements including DNA and RNA;

creating the context related algorithm at a computer device located in a second privileged computer network different from the privileged computer network, wherein the computer device residing outside of the privileged computer network also resides outside of the privileged computed network; and providing the context related algorithm to the computer device residing outside of the privileged computer network for storage and distribution to other privileged computer networks.

2. The method of claim 1, wherein context related algorithm is obtained automatically from the computer device residing outside of the privileged computer network.

3. The method of claim 1, further comprising,
selecting one or more sources whose context related algorithms obtained at the computer device; and
before obtaining the context related algorithm, verifying the context related algorithm stems from the selected one or more sources.

4. The method of claim 1, wherein the context related algorithm has been created at a computer device located in a second privileged computer network different from the privileged computer network, wherein the computer device residing outside of the privileged computer network also resides outside the second privileged computer network.

5. The method of claim 1, further comprising:
providing information regarding the result of the measurement to a computer device residing outside of the privileged computer network.

6. The method of claim 1, further comprising:
obtaining statistical information associated with the result of the measurement; and
adding the statistical information associated with the result of the measurement to the context specific supplement.

7. The method of claim 6, wherein the statistical information associated with the result of the measurement includes one or more of information regarding a likelihood of a combination of a measurement values in the result of the measurement with other measurement values, a likelihood of a combination of a measurement value in the result of the measurement with a particular diagnosis, a likelihood of a combination of a measurement value in the result with a particular disease progression or clinical finding, a likelihood of a combination of a measurement value in the result of the measurement with particular biometric data, statistical information regarding other measurements carried out in combination with the measurement having yielded the result.

8. The method of claim 1, wherein the information regarding the result of the measurement provided to a computer device residing outside of the privileged computer network includes one or more of one or more measurement values determined by the diagnostic or laboratory automated analyzer, one or more images obtained by the diagnostic or laboratory automated analyzers, a description of the result of the measurement of the diagnostic or laboratory automated analyzer and additional information associated with the result of the measurement.

9. The method of claim 1, wherein the information regarding the result of the measurement is anonymized.

10. The method of claim 1, wherein the one or more triggering conditions defines one or more criteria for the result of the measurement, optionally wherein the one or more criteria include one or more of a criterion evaluating a threshold for one or more measurement values, a criterion determining a relationship between two or more measurement values and a criterion defining a pattern in a result of a measurement.

11. The method of claim 1, wherein the privileged computer network including at least the computer device and the diagnostic or laboratory automated analyzer is protected by a firewall or other network protections.

* * * * *